United States Patent
Kamins et al.

(10) Patent No.: US 7,397,558 B2
(45) Date of Patent: Jul. 8, 2008

(54) ORDERED ARRAY OF NANOPARTICLES FOR EFFICIENT NANOENHANCED RAMAN SCATTERING DETECTION AND METHODS OF FORMING THE SAME

(75) Inventors: Theodore I. Kamins, Palo Alto, CA (US); Alexandre M. Bratkovski, Mountain View, CA (US); Shashank Sharma, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 313 days.

(21) Appl. No.: 11/084,833

(22) Filed: Mar. 17, 2005

(65) Prior Publication Data

US 2006/0209300 A1    Sep. 21, 2006

(51) Int. Cl.
  *G01J 3/44* (2006.01)
(52) U.S. Cl. ...................................................... 356/301
(58) Field of Classification Search ................... 356/301
  See application file for complete search history.

(56) References Cited

U.S. PATENT DOCUMENTS

| | | | |
|---|---|---|---|
| 4,674,878 A | 6/1987 | Vo-Dinh | |
| 4,944,985 A | 7/1990 | Alexander et al. | |
| 5,017,007 A | 5/1991 | Milne et al. | |
| 5,242,828 A | 9/1993 | Bergstrom et al. | |
| 5,255,067 A | 10/1993 | Carrabba et al. | |
| 5,527,712 A | 6/1996 | Sheehy | |
| 5,772,905 A | 6/1998 | Chou | |
| 5,837,552 A | 11/1998 | Cotton et al. | |
| 5,864,397 A | 1/1999 | VoDinh | |
| 5,885,753 A | 3/1999 | Crooks et al. | |
| 6,025,202 A | 2/2000 | Natan | |
| 6,149,868 A | 11/2000 | Natan et al. | |
| 6,165,911 A | 12/2000 | Calveley | |
| 6,242,264 B1 | 6/2001 | Natan et al. | |
| 6,248,674 B1 | 6/2001 | Kamins et al. | |
| 6,344,272 B1 * | 2/2002 | Oldenburg et al. | .......... 428/403 |
| 6,365,059 B1 | 4/2002 | Pechenik | |
| 6,406,777 B1 | 6/2002 | Boss et al. | |
| 6,432,740 B1 | 8/2002 | Chen | |
| 6,579,721 B1 | 6/2003 | Natan et al. | |

(Continued)

FOREIGN PATENT DOCUMENTS

WO    WO 98/10289 A1    3/1998

(Continued)

OTHER PUBLICATIONS

Drew, Christopher, et al., "Metal Oxide-Coated Polymer Nanofibers," Nano Lett., vol. 3, No. 2, pp. 143-147, 2003.

(Continued)

*Primary Examiner*—Patrick Connolly
*Assistant Examiner*—Scott M Richey

(57) ABSTRACT

Methods of forming NERS-active structures are disclosed that include ordered arrays of nanoparticles. Nanoparticles covered with an outer shell may be arranged in an ordered array on a substrate using Langmuir-Blodgett techniques. A portion of the outer shell may be removed, and the exposed nanoparticles may be used in a system to perform nanoenhanced Raman spectroscopy. An ordered array of nanoparticles may be used as a mask for forming islands of NERS-active material on a substrate. NERS-active structures and an NERS system that includes an NERS-active structure are also disclosed. Also disclosed are methods for performing NERS with NERS-active structures.

19 Claims, 7 Drawing Sheets

U.S. PATENT DOCUMENTS

| | | | |
|---|---|---|---|
| 6,623,977 | B1 | 9/2003 | Farquharson et al. |
| 6,649,683 | B2 | 11/2003 | Bell |
| 6,660,381 | B2 * | 12/2003 | Halas et al. .................. 428/403 |
| 6,773,616 | B1 | 8/2004 | Chen et al. |
| 7,057,732 | B2 | 6/2006 | Jorgenson et al. |
| 7,136,160 | B2 * | 11/2006 | Wang ........................ 356/301 |
| 7,151,599 | B2 * | 12/2006 | Islam et al. .................. 356/301 |
| 7,212,284 | B2 * | 5/2007 | Deng et al. .................. 356/301 |
| 2002/0142480 | A1 | 10/2002 | Natan |
| 2002/0155507 | A1 * | 10/2002 | Bruchez et al. ............... 435/7.2 |
| 2003/0059820 | A1 | 3/2003 | VoDinh |
| 2003/0120137 | A1 | 6/2003 | Pawluczyk |
| 2003/0157732 | A1 | 8/2003 | Baker et al. |
| 2003/0165418 | A1 | 9/2003 | Ajayan et al. |
| 2003/0174384 | A1 | 9/2003 | Halas et al. |
| 2003/0231304 | A1 | 12/2003 | Chan et al. |
| 2004/0077844 | A1 | 4/2004 | Jacobson et al. |
| 2004/0134778 | A1 | 7/2004 | Stelzle et al. |
| 2004/0135997 | A1 | 7/2004 | Chan et al. |
| 2004/0150818 | A1 | 8/2004 | Armstrong et al. |
| 2005/0142567 | A1 | 6/2005 | Su et al. |
| 2005/0255236 | A1 * | 11/2005 | Deng et al. .................. 427/180 |
| 2006/0017918 | A1 | 1/2006 | Cullum et al. |
| 2006/0054881 | A1 | 3/2006 | Li et al. |
| 2006/0164634 | A1 * | 7/2006 | Kamins et al. ............... 356/301 |
| 2006/0164636 | A1 * | 7/2006 | Islam et al. .................. 356/301 |
| 2006/0209300 | A1 | 9/2006 | Kamins et al. |

FOREIGN PATENT DOCUMENTS

WO   WO 2004/059279 A2   7/2004

OTHER PUBLICATIONS

Green, Mino, et al., "SERS Substrates Fabricated by Island Lithography: The Silver/Pyridine System," J. Phys. Chem. B, vol. 107, No. 47, pp. 13015-13021, 2003.

Kamins, T.I., et al., "Chemically vapor deposited Si nanowires and nucleated by self-assembled Ti islands on patterned and unpatterned Si substrates," Physica E 13, pp. 995-998, 2002.

Kneipp, Katrin, et al., "Single Molecule Detection Using Surface-Enhanced Raman Scattering (SERS)," Physical Review Letters, vol. 78, No. 9, pp. 1667-1670, Mar. 3, 1997.

Liu, Feng-Ming, et al., "Efficient SERS substrates made by electroless silver deposition into patterned silicon structures," J. Mater. Chem., 14, pp. 1526-1532, 2004.

Otto, Andreas, "Some Aspects of the Mechanisms of SERS," Heinrich-Heine-Universitat Dusseldorf, Lehrstuhl fur Oberflachenwissenschaft, Universitatsstr. 1, 40225 Dusseldorf, F.R. Germany, EU, e-mail: otto@rz.uni-duesseldorf.de, 4 pages, unknown date.

Otto, Andreas, "What is observed in single molecule SERS?," submitted to J. Raman Spectroscopy, Lehrstuhl fur Oberflachenwissenschaft, Heinrich-Heine-Universitat Dusseldorf, D 40225 Dusseldorf, FR Germany, EU, 4 pages, unknown date.

Pinto, N.J., et al., "Electroless Deposition of Thin Metallic Films on Polymer Fibers Prepared via Electrospinning," Polymer Preprints, 44(2), pp. 138-139, 2003.

Whang, Dongmok, et al., "Nanolithography Using Hierarchically Assembled Nanowire Masks," Nano Lett., vol. 3, No. 7, pp. 951-954, 2003.

Collier, C.P., et al., "Reversible Tunig of Silver Quantum Dot Monolayers Through the Metal-Insulator Transition," Science, vol. 277, pp. 1978-1981, Sep. 26, 1997.

Garcia, F.J., et al., "Collective Theory for Surface Enhanced Raman Scattering," Physical Review Letters, vol. 77, No. 6, pp. 1163-1166, Aug. 5, 1996.

Nie, Shuming, et al., "Probing Single Molecules and Single Nanoparticles by Surface-Enhanced Raman Scattering," Science, vol. 275, pp. 1102-1106, Feb. 21, 1997.

Michaels et al. "Surfaced Enhanced Raman Spectroscopy of Individual Rhodamine 6G Molecules on Large Ag Nanocrystals," J. Am. Chem. Soc. 121, 9932-39 (1999).

Wei et al., "Engineering 'Hot Spots' for Surface Enhanced Raman Scattering", Proceedings of SPIE vol. 5221 Plasmonics: Metallic Nanostructures and Their Optical Properties, pp. 92-98, (2003).

* cited by examiner

ORDERED ARRAY OF NANOPARTICLES FOR EFFICIENT NANOENHANCED RAMAN SCATTERING DETECTION AND METHODS OF FORMING THE SAME

FIELD OF THE INVENTION

The invention relates to nanoenhanced Raman scattering (NERS). More particularly, the invention relates to NERS-active structures, including features having nanoscale dimensions, methods for forming NERS-active structures, and methods for performing NERS using NERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against the frequency thereof. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the otherwise weak Raman signal for detection. Nanoenhanced Raman scattering (NERS) is a technique that allows for generation of a stronger Raman signal from an analyte relative to conventional Raman spectroscopy. In NERS, the analyte molecules are adsorbed onto, or placed adjacent to, an active metal surface or structure (an "NERS-active structure"). The interactions between the molecules and the active structure cause an increase in the strength of the Raman signal. The mechanism of Raman signal enhancement exhibited in NERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999)).

Several NERS-active structures have been employed in NERS techniques, including activated electrodes in electrolytic cells, activated metal colloid solutions, and activated metal substrates such as a roughened metal surface or metal "islands" formed on a substrate. For example, it has been shown that adsorbing analyte molecules onto or near a specially roughened metal surface made from gold or silver may enhance the effective Raman scattering intensity by factors of between $10^3$ and $10^6$ when averaged over the illuminated area of the sample.

Recently, NERS has been performed employing randomly oriented nanostructures, such as nanometer scale needles, particles, and wires, as opposed to a simple roughened metallic surface. The intensity of the Raman scattered photons from a molecule adsorbed on such a nanostructure may be increased by factors as high as $10^{14}$. Thus, the intensity of Raman scattered photons could be increased over what is obtained presently if there was a method for forming NERS-active structures that included nanoscale features having well controlled size, shape, location, and orientation. Also, the inability to produce such NERS-active structures is impeding research directed to completely understanding the enhancement mechanisms and, therefore, the ability to optimize the enhancement effect. In addition, NERS-active structures require significant time and money to fabricate. If these problems can be overcome, the performance of nanoscale electronics, optoelectronics, and molecular sensors may be significantly improved.

Accordingly, there is a need for NERS-active structures that include nanoscale features having well controlled size, shape, location, and orientation, and methods for their manufacture. In addition, there is a need for methods for producing high quantities of such NERS-active structures at relatively low cost.

BRIEF SUMMARY OF THE INVENTION

The present invention, in a number of embodiments, includes NERS-active structures, including features having nanoscale dimensions, methods for forming NERS-active structures, and methods for performing NERS using NERS-active structures.

An NERS-active structure is disclosed that includes a substrate, a two-dimensional array of nanoparticles usable for enhancing Raman scattered radiation in NERS, the two-dimensional array of nanoparticles affixed to the substrate, and an outer shell partially coating at least some nanoparticles of the two-dimensional array of nanoparticles.

An NERS system is disclosed that includes an NERS-active structure, a light source configured to irradiate light onto the NERS-active structure, and a detector configured to receive Raman-scattered light scattered by an analyte when the analyte is located adjacent the NERS-active structure. The NERS-active structure includes a substrate, a two-dimensional array of nanoparticles usable for enhancing Raman scattered radiation in NERS affixed to the substrate, and an outer shell partially coating at least some nanoparticles of the two-dimensional array of nanoparticles.

A method for performing NERS is disclosed that includes the steps of providing an NERS-active structure, placing an analyte adjacent the NERS-active structure, irradiating the analyte and the NERS-active structure with excitation radiation, and detecting Raman scattered radiation scattered by the analyte. The NERS-active structure includes a substrate, a two-dimensional array of nanoparticles usable for enhancing Raman scattered radiation in NERS affixed to the substrate, and an outer shell partially coating at least some nanoparticles of the two-dimensional array of nanoparticles.

Also disclosed is a method for forming an NERS-active structure. The method includes: providing a plurality of nanoparticles; coating each nanoparticle in the mixture of nanoparticles with an outer shell; forming a monolayer of the nanoparticles on a liquid surface; passing a substrate through the monolayer of nanoparticles on the liquid surface to transfer the monolayer of nanoparticles to a surface of the substrate; attaching the monolayer of nanoparticles to the surface of the substrate; and removing a portion of the outer shell from at least some nanoparticles of the monolayer of nanoparticles.

Another method for forming an NERS-active structure includes: providing a substrate having a surface; forming a hexagonally-packed monolayer of nanoparticles on the surface of the substrate, the hexagonally-packed monolayer of nanoparticles having openings between the nanoparticles; depositing an NERS-active material on the surface of the substrate in the openings between the nanoparticles to form islands of NERS-active material on the surface of the substrate; and removing the hexagonally-packed monolayer of nanoparticles.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes NERS-active structures including an ordered array of features having nanoscale dimensions, methods for forming NERS-active structures, NERS systems including NERS-active structures, and methods for performing NERS using such systems.

The methods disclosed herein are drawn to the fabrication of NERS-active structures, including nanoscale features, in an ordered array having well controlled size and spacing, which allows for improved enhancement of the Raman-scattered signal intensity.

The term "NERS-active structure" as used herein means a structure that is capable of increasing the number of Raman-scattered photons that are scattered by a molecule when the molecule is located adjacent to the structure, and the molecule and structure are subjected to electromagnetic radiation.

The term "NERS-active material" as used herein means a material that, when formed into appropriate geometries or configurations, is capable of increasing the number of Raman-scattered photons that are scattered by a molecule when the molecule is located adjacent the material, and the molecule and material are subjected to electromagnetic radiation. NERS-active materials can be used to form an NERS-active structure.

The term "nanoparticle" as used herein means a particle having cross-sectional dimensions of less than about 100 nanometers.

The term "analyte molecule" as used herein means a molecule upon which it is desired to perform NERS.

The term "ligand" as used herein means an atom, molecule, ion or functional group capable of attaching to one or more nanoparticles or a substrate.

It should be understood that the illustrations presented herein are not meant to be actual views of any particular NERS-active structure, but are merely idealized representations which are employed to describe the present invention. Additionally, for ease of discussion, elements common to FIGS. 1 through 14 retain the same numerical designation.

Figure 1:
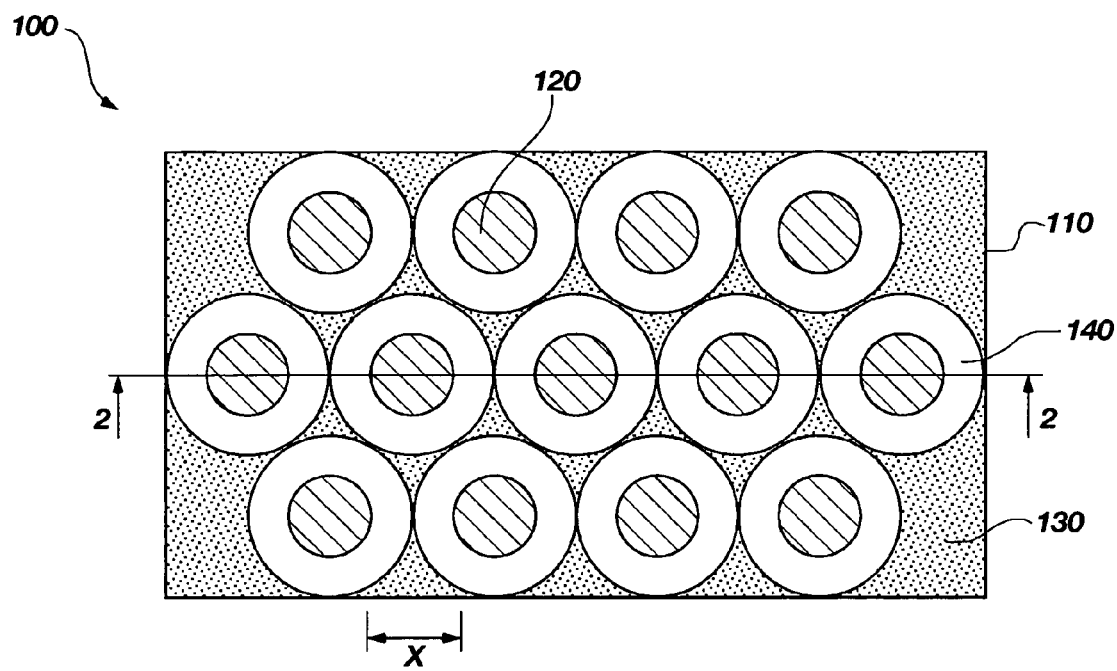
FIG. 1 is a top view of an exemplary embodiment of an NERS-active structure according to the invention.
Figure 2:
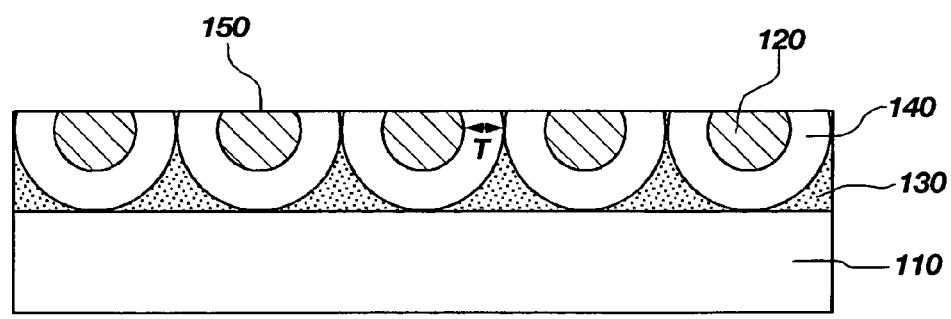
FIG. 2 is a cross-sectional view of the NERS-active structure of FIG. 1 taken along line 2-2.

An exemplary embodiment of an NERS-active structure according to the invention is shown in FIGS. 1 and 2. An NERS-active structure 100 includes a two-dimensional array of nanoparticles 120 disposed on a surface of a substrate 110. The nanoparticles 120 may have a generally spherical shape and a diameter of less than about 100 nanometers. More particularly, the nanoparticles 120 may have a diameter in a range from about 2 nanometers to about 20 nanometers.

Figure 5:
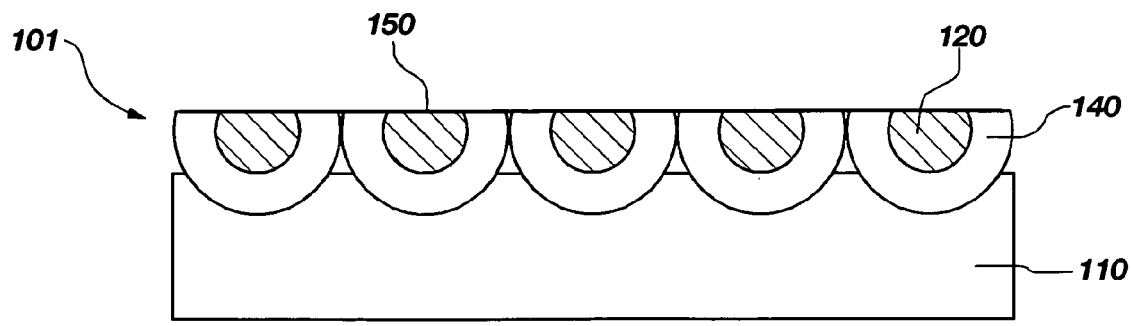

The nanoparticles 120 may be formed from, for example, gold, silver, copper, platinum, palladium, aluminum, or any other NERS-active material. The substrate 110 of the NERS-active structure 100 may be formed from, for example, plastic, silicon, silicon dioxide, silicon nitride, alumina, zirconia, tin oxide, or metal. Any suitable substrate material may be used, as long as the material does not fluoresce at the wavelength emitted by an excitation wavelength source employed in an NERS system. The nanoparticles 120 are affixed to the substrate 110 by a bonding material 130, such as a UV-curable polymer. Alternatively, the nanoparticles 120 may be embedded in the surface of the substrate 110, as shown in FIG. 5 and discussed herein below.

Nanoparticles 120 in the two-dimensional array of nanoparticles may be separated from adjacent nanoparticles 120 in the two-dimensional array by a distance X at their minimum spacing, that is, along a straight line passing through the centers of the adjacent nanoparticles 120. The distance X between adjacent nanoparticles 120 in the two-dimensional array of nanoparticles may be in a range from about 1 to about 100 nanometers. More particularly, the distance X may be in a range from about 1 to about 50 nanometers or alternatively in a range from about 0.5 to about 5 nanometers.

FIG. 2 is a cross-sectional view of the NERS-active structure 100 taken along section line 2-2 in FIG. 1. As seen in FIG. 2, portions of the nanoparticles 120 of the two-dimensional array of nanoparticles are coated with an outer shell 140. The outer shell 140 covers less than the entire surface area of each nanoparticle 120 such that the outer shell 140 covers approximately the lower surface area of each of the nanoparticles 120, leaving an exposed surface 150 of the nanoparticles 120. The outer shell 140 has a thickness T representing about half of the distance X between adjacent nanoparticles 120.

As seen in FIG. 2, the two-dimensional array of nanoparticles 120 of NERS-active structure 100 form a compact, ordered monolayer of nanoparticles on the surface of substrate 110.

Figure 3:
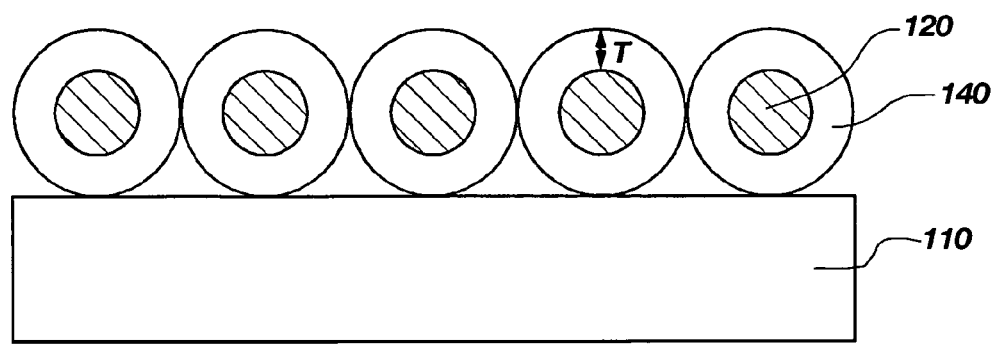
FIGS. 3-5 illustrate an exemplary method for forming another NERS-active structure of the present invention.
Figure 4:
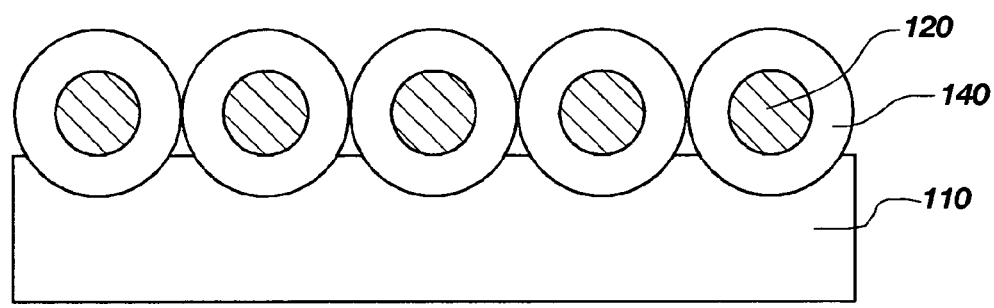

FIGS. 3-5 illustrate an exemplary method for forming an NERS-active structure that incorporates teachings of the present invention. The method includes use of Langmuir-Blodgett type techniques to form the monolayer of nanoparticles 120 on the surface of the substrate 110.

Commercially available preformed NERS-active metallic nanoparticles 120 may be provided and coated with an outer shell 140. The outer shell 140 may comprise organic ligands capable of attaching to the nanoparticles 120. Examples of organic ligands that will attach to the nanoparticles 120 include alkane thiol $HS(CH_2)_n$ chains with sulfur groups on one end), fluorophores, phosphate surfactants, and dendrimers. The outer shell has a thickness T equal to the length of the organic ligands, possibly modified by any deformation of the organic ligands. The length of the ligands thus determines the spacing between the nanoparticles 120. The distance X, as shown in FIG. 1, is twice the length of the organic ligands. The separation between adjacent nanoparticles 120 therefore may be controlled by providing organic ligands of the desired length. The separation between adjacent nanoparticles 120 may be such that the analyte molecule to be analyzed with the NERS-active structure 100 is capable of draping between two adjacent nanoparticles 120, part of the molecule being adsorbed on a first nanoparticle and another part of the molecule being adsorbed on a second, adjacent nanoparticle.

Alternatively, the outer shell 140 may comprise a sacrificial material surrounding the nanoparticles 120, such as an oxide or a sulfide. The thickness T of the outer shell 140 is selected to be half of the desired separation (i.e., the distance X) between adjacent nanoparticles 120. The distance X may be selected to correspond to the size of a particular analyte molecule to be analyzed with the NERS-active structure 100, such that the molecule is capable of being adsorbed between the nanoparticles 120. In yet another alternative, the outer shell 140 of at least some of the nanoparticles 120 may comprise a polymerizable or cross-linkable material.

The nanoparticles 120 may be formed into a compact, ordered array by Langmuir-Blodgett (LB) film deposition techniques or any suitable self-assembly technique. LB film deposition conventionally involves the process of creating (synthesizing) a monolayer of, for example, a molecular species or nanoparticles, on the surface of water or other suitable liquid. The monolayer may then be transferred to the surface of a substrate 110 by pulling the substrate from the monolayer-covered liquid. In the present case, this technique produces a substantially uniform monolayer of the nanoparticles 120 coated with the organic ligands 140 on the substrate 110, as seen in FIG. 3.

The substrate 110 shown in FIG. 4 may comprise a material, such as a plastic, that will soften when heated. The melting temperature of the substrate 110 is lower than the melting temperature of the nanoparticles 120 and the outer shell 140. The substrate 110 may be heated and softened, causing the nanoparticles 120 encased in the outer shell 140 to become embedded in the material of the substrate 110. The nanoparticles 120 are, thus, secured to the substrate 110.

At least a portion of the outer shell 140 may then be removed by suitable chemical and/or mechanical techniques, for example, chemical-mechanical polishing (CMP) or reactive ion etching (RIE), until the nanoparticles 120 are exposed, as shown in FIG. 5. A fraction of the nanoparticle 120 may be removed. The exposed surface 150 of the nanoparticles 120 provides an NERS-active structure 101.

Alternatively, nanoparticles 120 having an outer shell 140 of a polymerizable or cross-linkable material may be secured to the substrate 110 by curing the polymerizable or cross-linkable material, for example by exposing the polymerizable or cross-linkable material to ultraviolet radiation. The monolayer of nanoparticles 120 may include some nanoparticles 120 having an outer shell 140 of a polymerizable or cross-linkable material and some additional nanoparticles 120 having an outer shell 140 of an alternative material. The polymerizable or cross-linkable material may secure the entire monolayer of nanoparticles 120 to the substrate 110, as nanoparticles 120 adjacent to the polymerizable material-covered nanoparticles 120 are likewise adhered.

Figure 6:
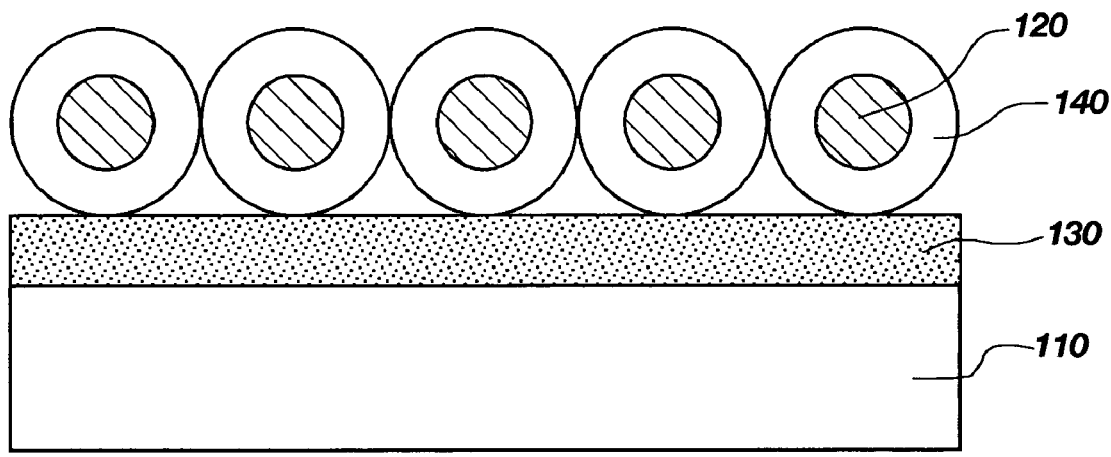
FIGS. 6-7 illustrate an exemplary method for forming the NERS-active structures of FIGS. 1 and 2.
Figure 7:
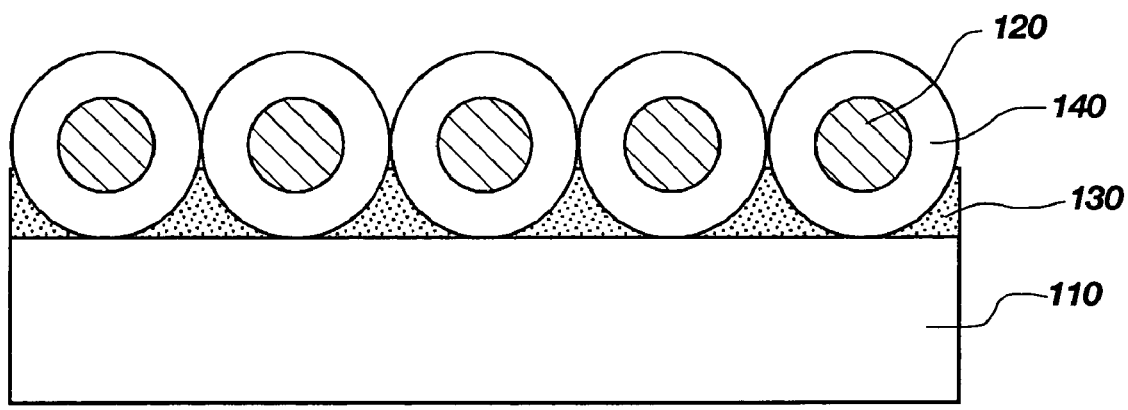

Another exemplary method for forming an NERS-active structure according to the invention is shown in FIGS. 6-7. A substrate 110 is provided, and covered with a polymerizable or cross-linkable material 130. The nanoparticles 120 may be coated with an outer shell 140 comprising organic ligands or a sacrificial material, and formed into a compact, ordered array by LB film deposition techniques. The monolayer may be transferred to the surface of the polymerizable or cross-linkable material 130 on the substrate 110 by pulling the substrate 110 covered with the polymerizable or cross-linkable material 130 from a monolayer-covered liquid. The nanoparticles 120, each encased in the outer shell 140, may be secured to the substrate 110 by curing the polymerizable or cross-linkable material 130, for example by exposing the polymerizable or cross-linkable material 130 to ultraviolet radiation.

At least a portion of the outer shell 140 may then be removed by suitable chemical and/or mechanical techniques. Exposing the nanoparticles 120 forms the NERS-active structure 100, shown in FIGS. 1 and 2.

Figure 8:
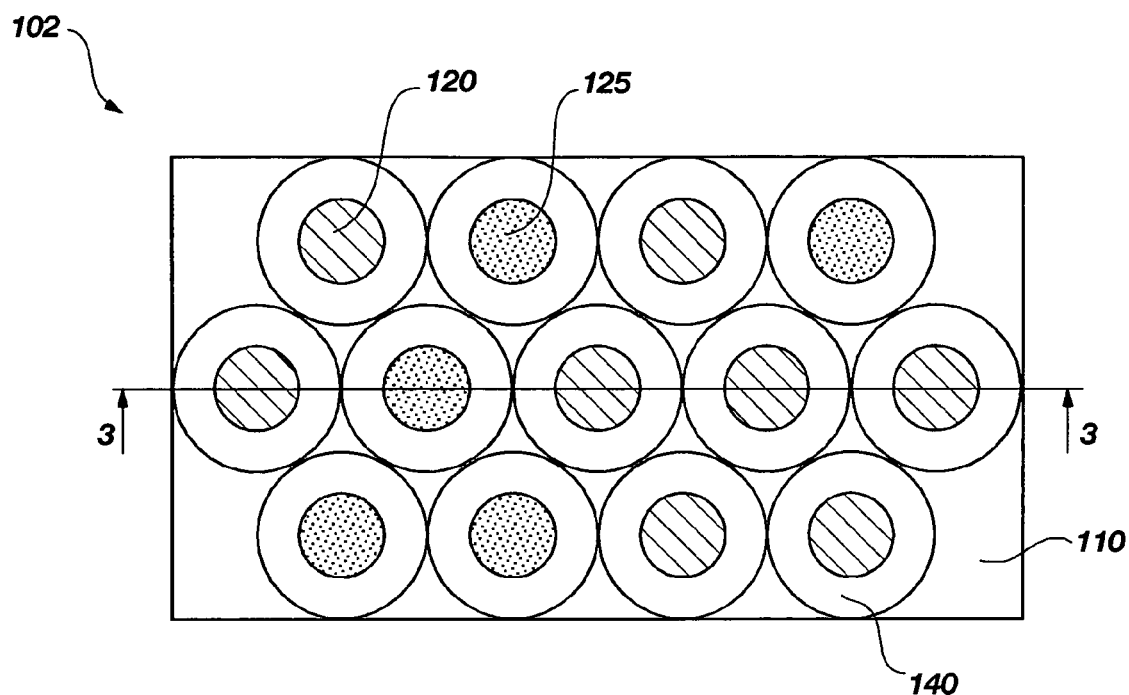
FIG. 8 is a top view of yet another exemplary embodiment of an NERS-active structure according to the invention.
Figure 9:
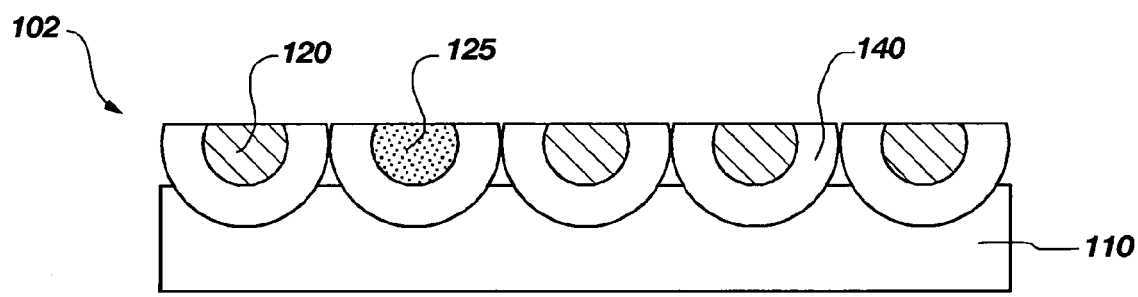
FIG. 9 is a cross-sectional view of the NERS-active structure of FIG. 8 taken along line 3-3.

Another exemplary embodiment of an NERS-active structure according to the invention is shown in FIG. 8. An NERS-active structure 102 includes a two-dimensional array of nanoparticles 120, 125 disposed on a surface of a substrate 110. A first plurality of the nanoparticles comprises active nanoparticles 120. A second plurality of the nanoparticles comprises inactive nanoparticles 125. The active nanoparticles 120 may be formed from, for example, gold, silver, copper, platinum, palladium, aluminum or any other NERS-active material. The inactive nanoparticles 125 may be formed from, for example, a dielectric such as silica ($SiO_2$), alumina ($Al_2O_3$), cobalt, or any other material that either does not exhibit a plasmon frequency, or that exhibits a plasmon frequency differing from the plasmon frequency exhibited by the active nanoparticles 120, such that isolated surface plasmon modes may exist in the regions of the active nanoparticles 120 without generating surface plasmon modes in the regions of the inactive nanoparticles 125. The plasmon resonance can easily be observed in nanoparticles. In particular, the electric dipole response has been well studied. Dielectric particles are inactive because they do not have the plasmon resonance and accompanying strong increase in a local electric field necessary for the observation of the NERS. Cobalt particles will likely oxidize and form CoO oxide shells or oxidize completely. This will make them inactive, shifting the resonance away from that in NERS active particles.

The active nanoparticles 120 and the inactive nanoparticles 125 may be coated with an outer shell 140 comprising organic ligands or a sacrificial material, and formed into an ordered array on the substrate 110 by LB film deposition techniques. Optionally, the substrate may be covered with a polymerizable or cross-linkable material (not shown). The active nanoparticles 120 and the inactive nanoparticles 125 may be secured to the substrate by heating, or by curing the polymerizable or cross-linkable material. Portions of the outer shell 140 may be removed, exposing the active nanoparticles 120 and the inactive nanoparticles 125, and forming the NERS-active structure 102.

Figure 10:
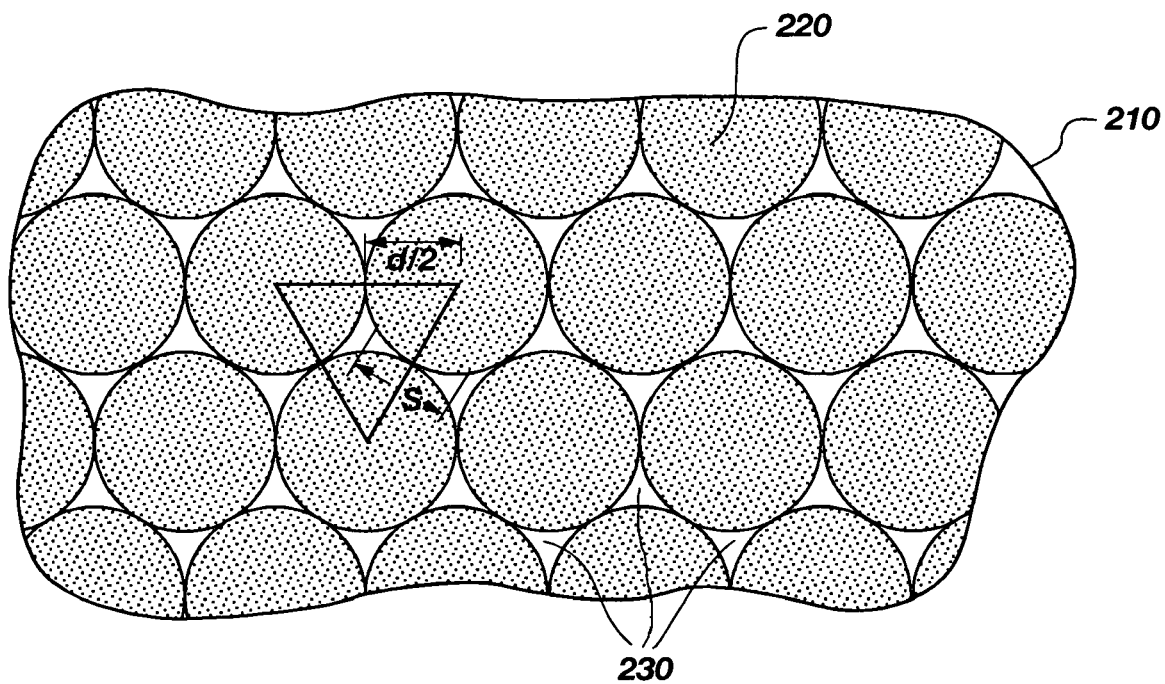
FIG. 10-12 illustrate another exemplary method for forming an NERS-active structure of the present invention.
Figure 11:
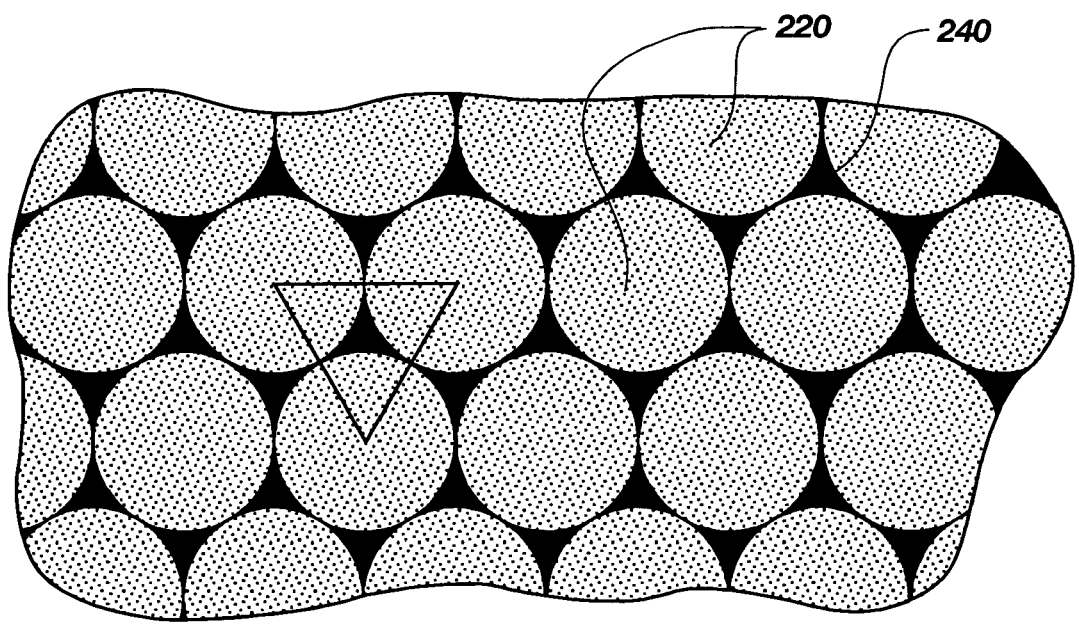

Still another exemplary method for making an NERS-active structure is illustrated in FIGS. 10-11. To produce the NERS-active structure, a substrate 210 may be provided. A partial section of the substrate 210 is shown in FIG. 10. A hexagonally closed packed assembly of nanoparticles 220 may be formed on a surface of the substrate 210 by any suitable method, for example, by LB film deposition techniques or by any suitable self-assembly technique. The assembly of nanoparticles 220 may be used as a shadow mask for deposition, forming nanoscale features. Openings 230 between the nanoparticles 220 provide access to the surface of the substrate 210, on which the nanoscale features may be formed.

As shown in FIG. 11, a material 240 of the feature to be formed, such as an NERS-active material, may be applied to the substrate 210 through the openings 230 by a conventional deposition technique including, but not limited to, chemical vapor deposition (CVD), physical vapor deposition (PVD), sputtering, or evaporation. The currently preferred method of deposition is a line-of-sight, non-conformal deposition. A non-conformal deposition technique deposits more material on horizontal surfaces, in this case the substrate 210, than on side or curved surfaces, in this case the nanoparticles 220. A portion of the material 240 may be deposited on the nanoparticles 220; however, this portion of the material 240 is not shown in FIG. 11 for clarity.

Figure 12:
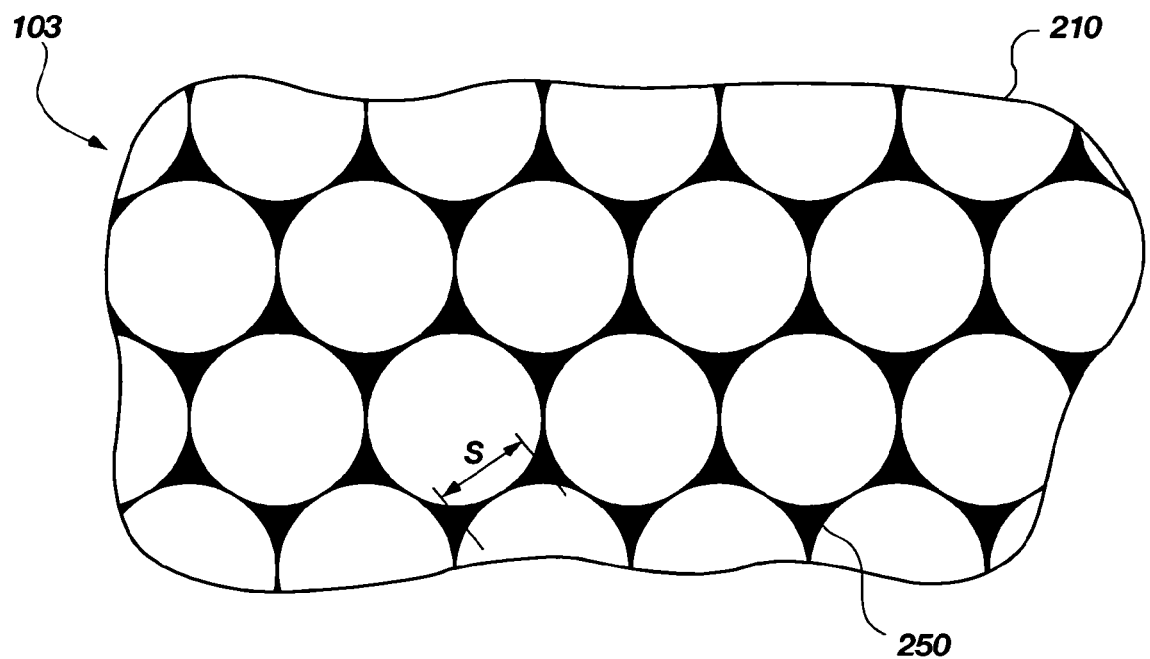

The nanoparticles 220 are removed, along with any material 240 deposited on the nanoparticles 220, leaving features 250 on the substrate 210, forming the NERS-active structure 103 of FIG. 12. The nanoparticles may be loosely adhered to the substrate 210, and may be washed off the substrate 210. Optionally, if the nanoparticles 220 are firmly adhered to the substrate 210, a highly selective chemical etch may be used to remove the nanoparticles 220.

The center-to-center spacing S of the features 250 is determined by the diameter d of the nanoparticles 220. Referring to FIG. 10, the center of the feature 250 will be the point equidistant from the centers of the three surrounding nanoparticles 220. The spacing S will be $2*d/(2*\sqrt{3})$. In other words, $S=d/\sqrt{3}$, or approximately d/1.732. In one exemplary embodiment, for a feature spacing S of three nanometers, nanoparticles having a diameter d of approximately five nanometers will be used.

The features 250 of FIG. 12 may also be employed as nuclei for further growth. The features grown may have an increased size and a decreased distance of separation, from outer perimeter to outer perimeter. The features 250 may optionally be etched, creating features of a decreased size and an increased distance of perimeter-to-perimeter spacing.

Figure 13:
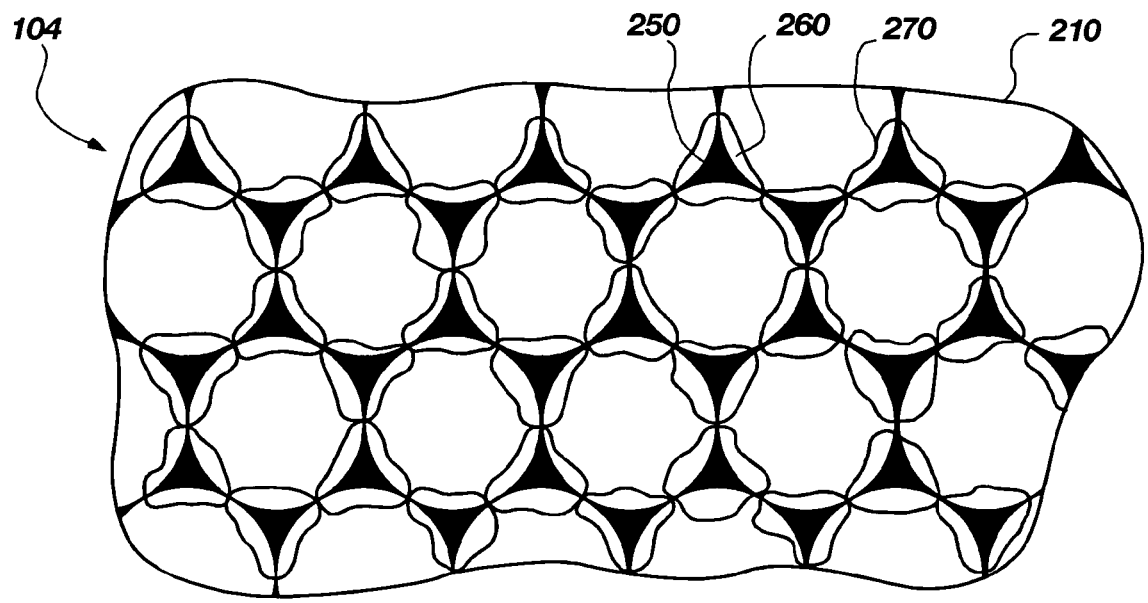
FIG. 13 is a top view of still another exemplary embodiment of an NERS-active structure according to the invention.

Yet another embodiment of an NERS-active structure 104 is shown in FIG. 13. The features 250 of FIG. 12 form the cores of an assembly of core-shell nanostructures 270. A shell 260 may surround each feature 250. One exemplary embodiment of a core-shell nanostructure is a core 250 of platinum and a shell 260 of cobalt. The NERS-active structure 104 may be used in an NERS system to enhance the Raman signal of an analyte.

Figure 14:
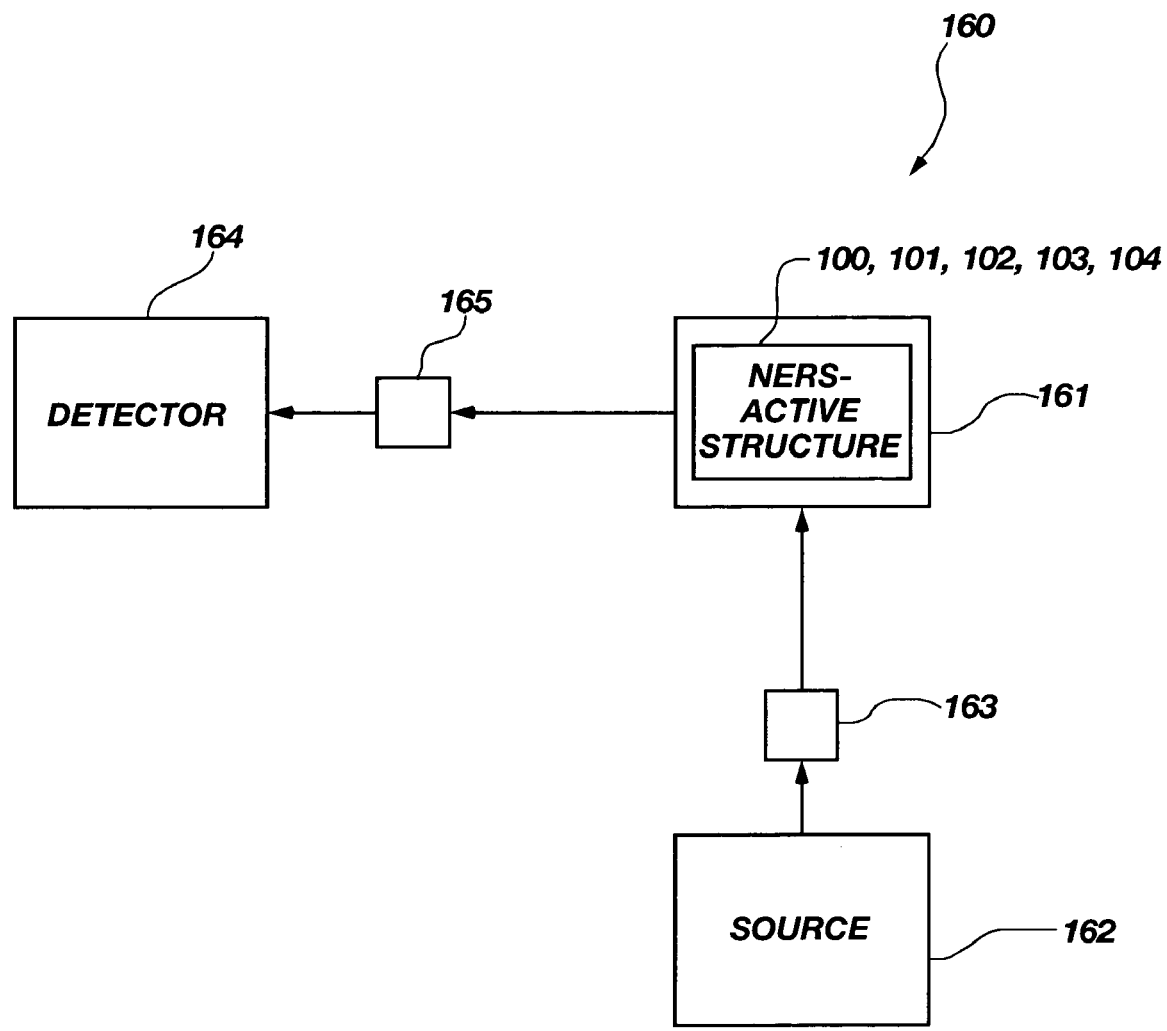
FIG. 14 is a schematic diagram of an exemplary system for performing nanoenhanced Raman spectroscopy using the NERS-active structures of FIGS. 1, 2, 5, 8, 9, 12, and 13.

An exemplary NERS system 160 according to the invention is illustrated schematically in FIG. 14. The system 160 may include one of the exemplary NERS-active structures 100, 101, 102, 103, and 104, and may be used to perform nanonhanced Raman spectroscopy. The NERS system 160 may include a sample or analyte stage 161, an excitation radiation source 162, and a detector 164. The analyte stage 161 may include one of the NERS-active structures 100, 101, 102, 103, and 104 (FIGS. 1-2, 5, 9, 12 and 13). The NERS system 160 also may include various optical components 163 positioned between the excitation radiation source 162 and the analyte stage 161, and various optical components 165 positioned between the analyte stage 161 and the detector 164.

The excitation radiation source 162 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation-emitting sources may be used as the excitation radiation source 162. The wavelengths that are emitted by the excitation radiation source 162 may be any suitable wavelength for analyzing the analyte using NERS. An exemplary range of wavelengths that may be emitted by the excitation radiation source 162 includes wavelengths between about 350 nm and about 1000 nm.

The excitation radiation emitted by the source 162 may be delivered either directly from the source 162 to the analyte stage 161 and the NERS-active structure 100, 101, 102, 103, 104. Alternatively, collimation, filtration, and subsequent focusing of the excitation radiation may be performed by optical components 163 before the excitation radiation impinges on the analyte stage 161 and the NERS-active structure 100, 101, 102, 103, 104.

The NERS-active structure 100, 101, 102, 103, 104 of the analyte stage 161 may enhance the Raman signal of the analyte, as discussed previously herein. In other words, irradiation of the NERS-active structure 100, 101, 102, 103, 104 by excitation radiation may increase the number photons inelastically scattered by an analyte molecule positioned near or adjacent to the NERS-active structure 100, 101, 102, 103, 104.

The Raman scattered photons may be collimated, filtered, or focused with optical components 165. For example, a filter or a plurality of filters may be employed, either as part of the structure of the detector 164, or as a separate unit that is configured to filter the wavelength of the excitation radiation, thus allowing only the Raman scattered photons to be received by the detector 164.

The detector 164 receives and detects the Raman scattered photons and may include a monochromator (or any other suitable device for determining the wavelength of the Raman scattered photons) and a device such as, for example, a photomultiplier for determining the quantity of Raman scattered photons (intensity).

Ideally, the Raman scattered photons are scattered isotropically, being scattered in all directions relative to the analyte stage 161. Thus, the position of the detector 164 relative to the analyte stage 161 is not particularly important. However, the detector 164 may be positioned at, for example, an angle of 90° relative to the direction of the incident excitation radiation to minimize the intensity of the incident excitation radiation that may be incident on the detector 164.

To perform NERS using the system 160, a user may provide an analyte molecule or molecules adjacent to the nanoscale components of the NERS-active structure 100, 101, 102, 103, 104. The analyte and the NERS-active structure 100, 101, 102, 103, 104 are irradiated with excitation radiation or light from the source 162. Raman scattered photons scattered by the analyte are then detected by the detector 164.

The structures and systems disclosed herein may also be used to perform enhanced hyper-Raman spectroscopy. When excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may have a frequency that is Raman-shifted relative to the frequencies corresponding to the higher order harmonics of the excitation radiation. These higher order Raman-scattered photons can provide information about the analyte molecule that cannot be obtained by first order Raman spectroscopy. Hyper-Raman spectroscopy involves the collection and analysis of these higher order Raman-scattered photons.

The methods disclosed herein allow for the reproducible formation of NERS-active structures, including nanoscale features having well controlled size, shape, location, and orientation. These structures allow for improved nanoenhanced Raman spectroscopy and may be used to produce molecular sensors having superior sensitivity relative to conventional NERS-active structures. The performance of nanoscale electronics, optoelectronics, molecular sensors, and other devices employing the Raman effect may be significantly improved by using the NERS-active structures disclosed herein. In addition, the methods disclosed herein allow for production of high quantities of NERS-active structures/materials at relatively low cost.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. An NERS-active structure comprising:
   a substrate;
   a two-dimensional array of nanoparticles usable for enhancing Raman scattered radiation, the two-dimensional array of nanoparticles affixed to the substrate; and
   an outer shell partially coating at least some nanoparticles of the two-dimensional array of nanoparticles, wherein each coated nanoparticle of the two-dimensional array of nanoparticles is separated from adjacent nanoparticles by a predetermined distance.

2. The NERS-active structure of claim 1, further comprising a bonding material between the substrate and the two-dimensional array of nanoparticles.

3. The NERS-active structure of claim 2 wherein the bonding material comprises a UV-curable polymer.

4. The NERS-active structure of claim 1, wherein the two-dimensional array of nanoparticles is embedded in the substrate.

5. The NERS-active structure of claim 4, wherein the substrate comprises plastic.

6. The NERS-active structure of claim 1, wherein the two-dimensional array of nanoparticles includes a plurality of active nanoparticles and a plurality of inactive nanoparticles, the plurality of inactive nanoparticles exhibiting a plasmon frequency differing from the plasmon frequency exhibited by the plurality of active nanoparticles.

7. The NERS-active structure of claim 1, wherein the outer shell comprises organic ligands.

8. The NERS-active structure of claim 1, wherein the outer shell comprises a sacrificial material.

9. The NERS-active structure of claim 8, wherein the sacrificial material comprises one of an oxide and a sulfide.

10. The NERS-active structure of claim 1, wherein the outer shell comprises organic ligands having a length, and the predetermined distance is substantially equal to twice the length of the organic ligands.

11. The NERS-active structure of claim 1, wherein the outer shell comprises a sacrificial material having a thickness, and the predetermined distance is substantially equal to twice the thickness of the sacrificial material.

12. An NERS-active structure comprising:
   a substrate;
   a two-dimensional array of nanoparticles usable for enhancing Raman scattered radiation, the two-dimensional array of nanoparticles affixed to the substrate;
   an outer shell partially coating at least some nanoparticles of the two-dimensional array of nanoparticles; and
   an analyte molecule adsorbed between two nanoparticles of the two-dimensional array of nanoparticles.

13. The NERS-active structure of claim 1, wherein each nanoparticle of the two-dimensional array of nanoparticles has a generally spherical shape and an average diameter of less than about 100 nm.

14. The NERS-active structure of claim 1, wherein each nanoparticle of the two-dimensional array of nanoparticles has an average diameter within a range from about 1 nanometer to about 25 nanometers.

15. The NERS-active structure of claim 1, wherein the substrate comprises one of plastic, silicon, silicon dioxide, silicon nitride, alumina, zirconia, tin oxide, and metal.

16. The NERS-active structure of claim 1, wherein at least some nanoparticles of the two-dimensional array of nanoparticles comprise one or more of gold, silver, copper, platinum, palladium, and aluminum.

17. An NERS system comprising:
   an NERS-active structure comprising:
   a substrate;

a two-dimensional array of nanoparticles usable for enhancing Raman scattered radiation in NERS, the two-dimensional array of nanoparticles affixed to the substrate; and an outer shell partially coating at least some nanoparticles of the two-dimensional array of nanoparticles;

a light source configured to irradiate light onto the NERS-active structure; and a detector configured to receive Raman-scattered light scattered by an analyte located adjacent the NERS-active structure.

18. A method for performing NERS comprising:

providing an NERS-active structure comprising:

a substrate;

a two-dimensional array of nanoparticles usable for enhancing Raman scattered radiation in NERS affixed to the substrate; and an outer shell partially coating at least some nanoparticles of the two-dimensional array of nanoparticles;

placing an analyte adjacent to the NERS-active structure;

irradiating the analyte and the NERS-active structure with excitation radiation; and detecting Raman scattered radiation scattered by the analyte.

19. The method of claim 18 wherein the step of detecting comprises detecting Raman scattered radiation scattered by a single molecule.

* * * * *